US00PP24319P3

(12) United States Plant Patent
Schoone

(10) Patent No.: US PP24,319 P3
(45) Date of Patent: Mar. 18, 2014

(54) ***PHALAENOPSIS* ORCHID PLANT NAMED 'BABY SEAL'**

(50) Latin Name: ***Phalaenopsis* hybrid**
Varietal Denomination: Baby Seal

(75) Inventor: René Schoone, Assendelft (NL)

(73) Assignee: Floricultura, Heemskerk (NE)

( * ) Notice: Subject to any disclaimer, the term of this patent is extended or adjusted under 35 U.S.C. 154(b) by 1 day.

(21) Appl. No.: 13/506,416

(22) Filed: Apr. 18, 2012

(65) Prior Publication Data

US 2012/0272423 P1 Oct. 25, 2012

Related U.S. Application Data

(60) Provisional application No. 61/478,813, filed on Apr. 25, 2011.

(30) Foreign Application Priority Data

Apr. 27, 2011 (NL) ..... PBR OPS795

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP

(57) ABSTRACT

A new and distinct *Phalaenopsis* plant named 'Baby Seal' particularly characterized by flowers which are white; within the labellum some yellow and purple; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Baby Seal'.

CROSS-REFERENCE TO RELATED APPLICATIONS

This application claims priority to U.S. Provisional Application No. 61/478,813, filed Apr. 25, 2011 and Netherlands Plant Breeders' Rights Application No. OPS795, filed Apr. 27, 2011. The disclosure of both prior applications are hereby incorporated by reference in their entirety.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Baby Seal'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Baby Seal' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Baby Seal' originated from a cross made by the inventor in 1998 in Strengweg, Heemskerk, The Netherlands. The female or seed parent is the *Phalaenopsis* cultivar designated 'Sogo Yukidian', unpatented. The male or pollen parent is the *Phalaenopsis* cultivar designated 'World Class', unpatented. The new *Phalaenopsis* 'Baby Seal' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in November, 2006 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Baby Seal', which in combination distinguish this *Phalaenopsis* as a new and distinct cultivar:

1. flowers which are white; within the labellum some yellow and purple;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Baby Seal', the female parent 'Sogo Yukidian' has white flowers and they are about 12 cm in size, the male parent 'World Class' has white colored flowers and they are about 10 cm in size, whereas the flowers of 'Baby Seal' are white and are about 11 cm in size.

Presently, there is no commercial cultivar to which 'Baby Seal' can be meaningfully compared.

BRIEF DESCRIPTION OF THE PHOTOGRAPHS

The accompanying photographs illustrate the overall appearance of the new *Phalaenopsis* 'Baby Seal' showing the colors as true as is reasonably possible with colored reproductions of this type. Colors in the photographs may differ slightly from the color values cited in the detailed botanical description, which accurately describe the color of 'Baby Seal'.

DETAILED BOTANICAL DESCRIPTION

Figure 1:
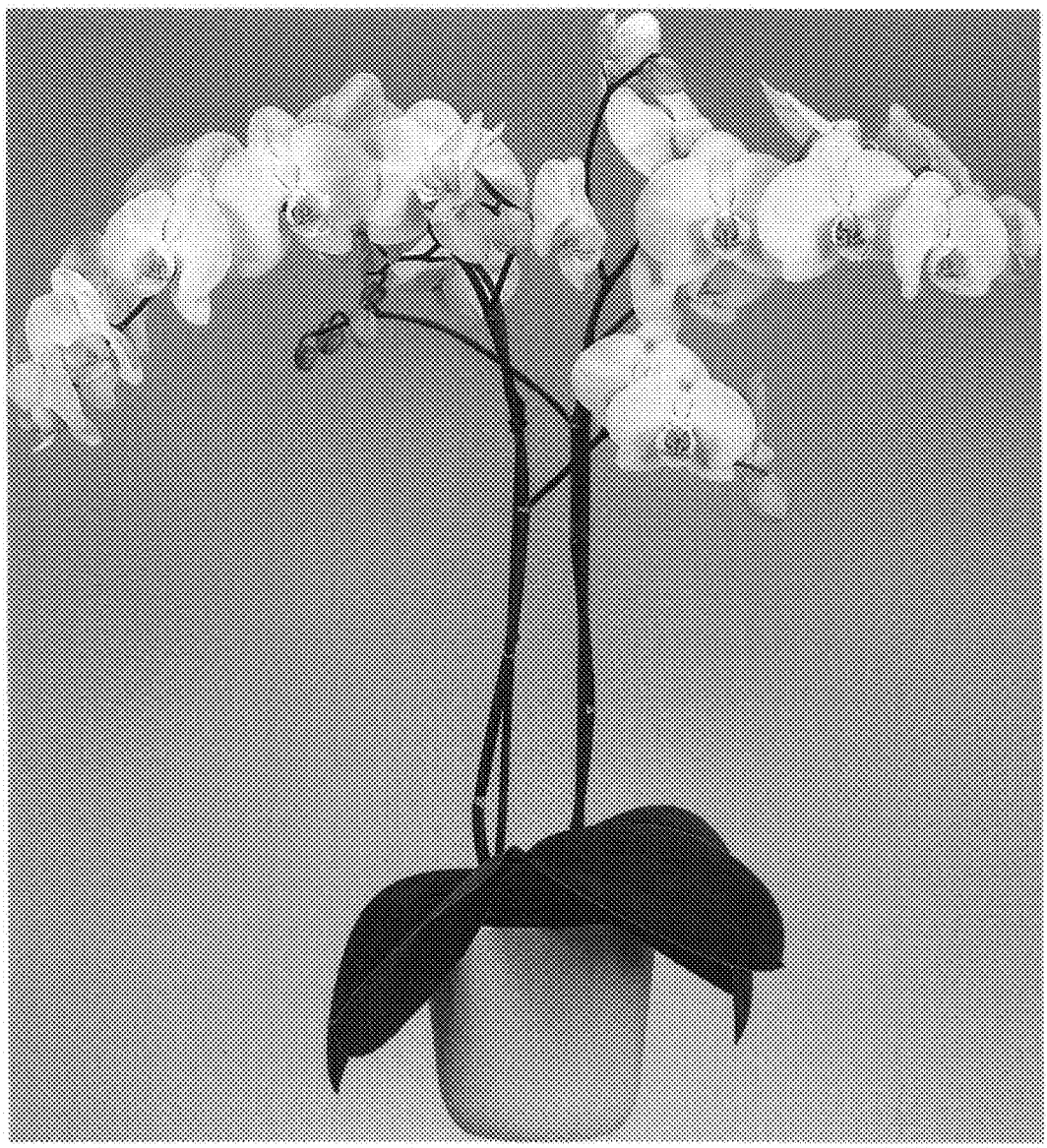
FIG. 1 shows a side view perspective of a typical flowering plant of 'Baby Seal' in a 12 cm pot, at 16 months of age.

The new *Phalaenopsis* cultivar 'Baby Seal' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Baby Seal' as grown in a greenhouse in Strengweg, Heemskerk, The Netherlands, under conditions which closely approximate those generally used in commercial practice. Initially, the ideal temperature to grow plants of 'Baby Seal' is 27° C. during the day and at night. Then, during the flowering phase of 'Baby Seal', the ideal growing temperature is 20-22° C. during the day and 18° C. at night. Light levels for growing 'Baby Seal' are a minimum of 5,000 lux and a maximum of 10,000 lux. A balanced fertilizer with level of 200 ppm N, 87 ppm P, 168 ppm K is applied. Duration of growth of 'Baby Seal' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Baby Seal' plants described is 12 months after potting.

Classification:

*Botanical.*—*Phalaenopsis* hybrid.

Parentage:

*Female or seed parent.*—*Phalaenopsis* cultivar designated 'Sogo Yukidian', unpatented.

*Male or pollen parent.*—*Phalaenopsis* cultivar designated 'World Class', unpatented.

Propagation:

*Type.*—Tissue culture.

*Rooting habit and description.*—Approximately 5 mm-7 mm wide and greyed/green (RHS 190B and RHS 195A) in color; freely branching. It takes 12 weeks for plants growing in tissue culture to initiate roots.

Plant:

*Size at maturity.*—Height: about 67 cm. Spread: about 40 to 50 cm.

*Growth habit.*—Standard; green (RHS N137B) leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture* (*upper and under surface*).—Smooth and leathery.

*Pubescence.*—None.

*Mature leaf length.*—About 15 to 25 cm.

*Mature leaf width.*—About 7 to 9 cm.

*Mature leaf thickness.*—About 2 mm.

*Mature leaf color.*—Upper side: green, RHS N137B. Under side: green, RHS 137C.

*Leaf base.*—Acute.

*Margin.*—Entire.

*Venation.*—Pattern: parallel. Color of midvein: Upper side: green, RHS N137B. Under side: green, RHS 137C.

Raceme:

*Quantity per plant.*—About 1 to 2.

*Number of flowers per raceme.*—About 5 to 10.

*Length.*—About 65 to 70 cm.

*Diameter.*—About 5 mm.

*Strength.*—Strong.

*Aspect.*—Upright.

*Texture.*—Glabrous and smooth.

*Color.*—A combination of brown (RHS N200A) with yellow-green spots (RHS 144B).

*Internode.*—Length: about 35 mm and 45 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 to 25 mm. Diameter (at midpoint): about 15 to 25 mm. Shape: egg-shaped. Color: yellow-green RHS 145C with some purple RHS N79C.

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
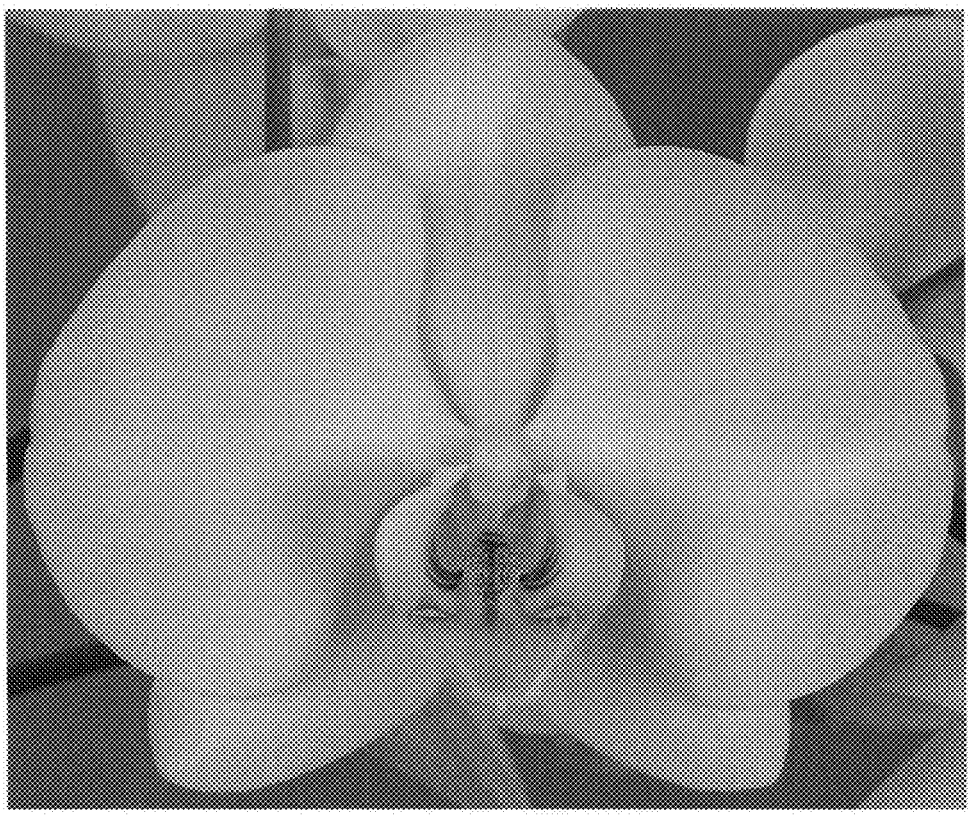
FIG. 2 shows a close-up view of the typical buds and flowers of 'Baby Seal'.
Figure 3:
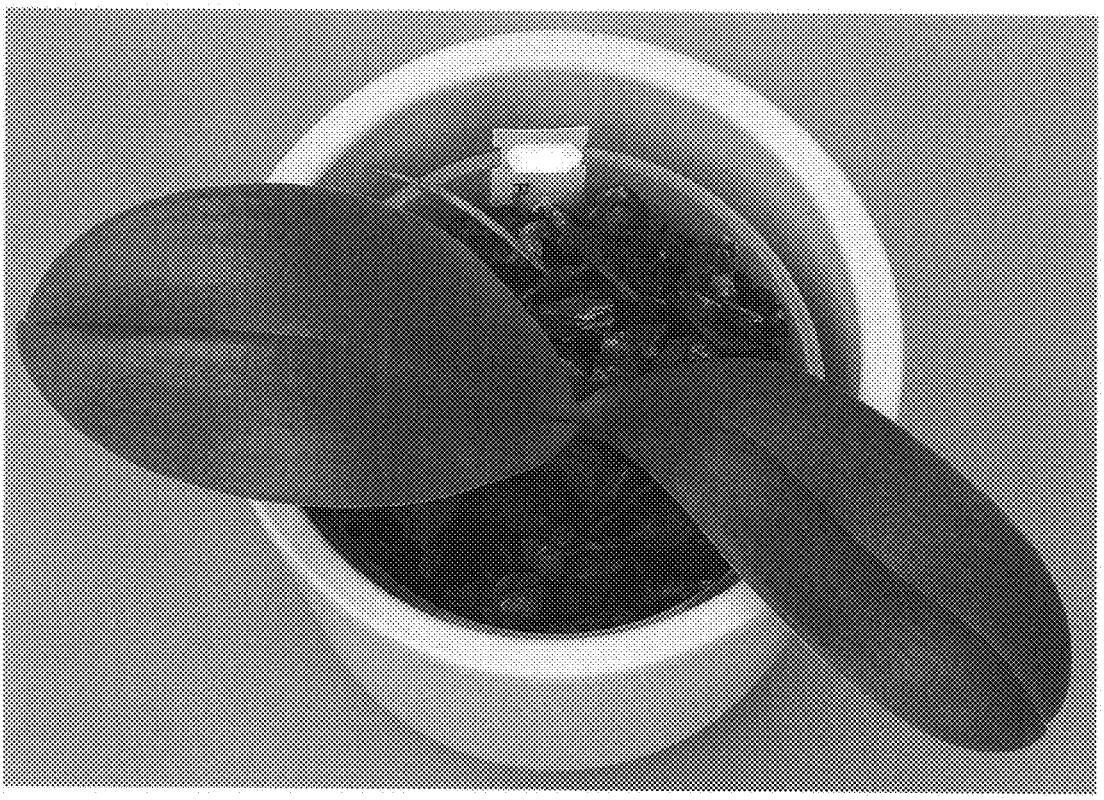
FIG. 3 shows a close-up view of the typical leaves of 'Baby Seal'.

*Flower.*—Rate of opening: Flowers fully opened about 2 to 3 days after petal and sepal separation. Orientation at opening: slanted upward and outward. Shape: Typical shape of *phalaenopsis* orchid; see FIG. 2. Size: Height: about 90 mm. Diameter: about 110 mm. Depth of tube: about 20 mm.

*Petals.*—Quantity and arrangement: six petals and sepals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate and weakly cupped. Apex: oval. Margin: entire and weakly undulate. Base: broadly ovate. Length: about 70 mm. Width: about 50 mm. Texture: Upper surface: smooth and satiny. Under surface: smooth and satiny. Color (when fully opened): upper & under surface: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: oval. Length: about 20 mm. Width (not flattened): about 25 mm. Texture: Upper and under surface: smooth and satiny. Color (when fully opened): Upper surface: Midlobe: The main color is white (RHS NN155C). The top edges of the midlobe are greyed-orange (RHS 171A). The corners on the sides are yellow (RHS 2B). Also little yellow in center at the base. Lateral lobes: main color is white (RHS NN155C). At the base are red-purple stripes (RHS 71A). Lower edge close to the base greyed-orange (RHS 171A) and then yellow (RHS 2B). Under surface: Midlobe: main color is white (RHS NN155C). At the corners some green-yellow (RHS 1B) and at the base some greyed-orange (RHS 171B). Lateral lobes: main color is white (RHS N155C). Bottom edges are green-yellow (RHS 1B). Closer to the base also some greyed-orange (RHS 171B) on the edges. Chirri: about 26 mm. color: white (RHS NN155C) with yellow (RHS 2B) on the end. Pestle (Callosities): Length: about 4 mm. Width (not flattened): about 6 mm. Color: yellow (RHS 9B) with red-purple spots and stripes (RHS 71A).

*Sepals.*—Arrangement: Outer whorl comprises 3 sepals. Overall shape: elliptical and weakly cupped. Margin: entire and weakly undulate. Length: about 50 mm to 60 mm. Width: about 30 mm to 40 mm. Apex: oval/round. Texture: Upper and under surface: smooth and satiny. Color (when fully opened): upper surface: white (RHS NN155C). At the base of the lateral sepals is green-yellow haze (RHS 1D) spread over the ground color. Under surface: white (RHS NN155C) with a haze of green-yellow (RHS 1D) and red-purple (RHS 64B) at the base, spread over the ground color.

*Pedicel.*—Length: about 40 mm. Diameter: about 3 mm. Texture: glabrous and smooth. Color: yellow-green RHS 145C with RHS 146C.

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 8 mm. Diameter: about 7 mm. Color: white (RHS NN155C).

*Pollinia.*—Quantity: Two. Diameter: about 1 mm. Color: orange (RHS N25A).

*Ovary.*—Length: about 5 mm. Diameter: about 6 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Baby Seal', as illustrated and described herein.

* * * * *